United States Patent [19]
Peyman et al.

[11] Patent Number: 5,527,356
[45] Date of Patent: Jun. 18, 1996

[54] RETINAL PLUG

[75] Inventors: Gholam A. Peyman, New Orleans; Dachuan Yang, Metiarie, both of La.

[73] Assignee: Syntec, Inc., Winfield, Mo.

[21] Appl. No.: 424,882

[22] Filed: Apr. 19, 1995

Related U.S. Application Data

[63] Continuation-in-part of Ser. No. 284,906, Aug. 2, 1994.
[51] Int. Cl.$^6$ ........................................................ A61F 2/14
[52] U.S. Cl. ................................................. 623/4; 128/898
[58] Field of Search ................................. 623/4; 128/898

[56] References Cited

PUBLICATIONS

M. B. Bornstein, M.D., Reconstituted Rat–Tail Collagen Used as Substrate for Tissue Cultures on Coverslips in Maximow Slides and Roller Tubes, vol. 7, No. 2; 1958, pp. 134–137, Laboratory Investigations.

Michalopoulos and Pitot, Primary Culture of Parenchymal Liver Cells on Collagen Membranes, Experimental Cell Research 94 (1975) pp. 70–78.

C. A. Le Bourlais, et al, New Ophthamic Drug Delivery Systems, Drug Development and Industrial Pharmacy, 21(1), (1955) pp. 19, 33–36.

*Primary Examiner*—Randy C. Shay
*Attorney, Agent, or Firm*—Polster, Lieder, Woodruff & Lucchesi

[57] ABSTRACT

A plug for repairing a defect in the retina. The plug can be made from a biodegradable, non-biodegradable, natural or synthetic material. The plug is dimensioned to fit the defect during a vitrectomy procedure to prevent ingress of vitreous fluid into the subretinal space and prevent the migration of pigmented retinal cells. The plug can be formed from a solution that gels at body temperature to form a plug.

6 Claims, 4 Drawing Sheets

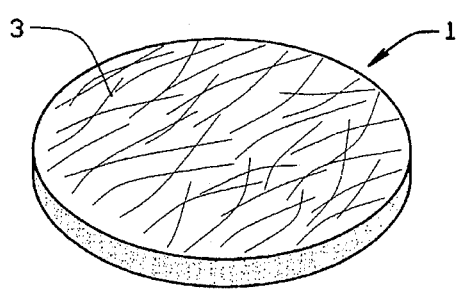
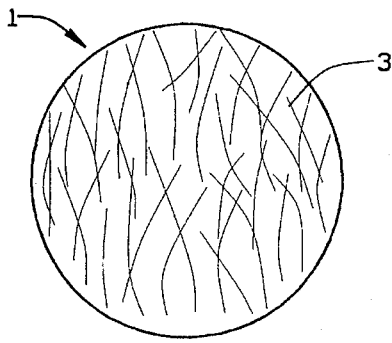
FIG. 1　　FIG. 2
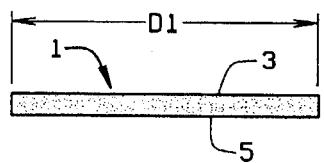
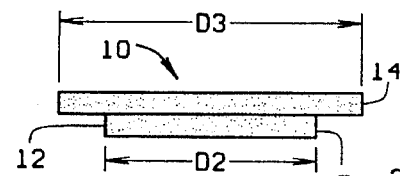
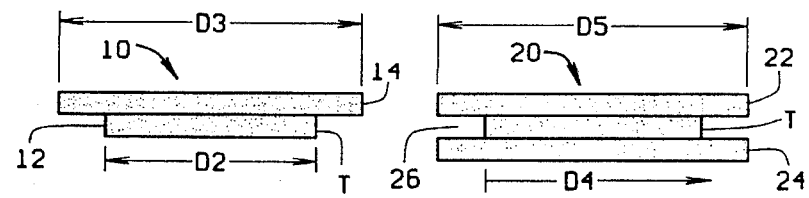
FIG. 3　　FIG. 4　　FIG. 5
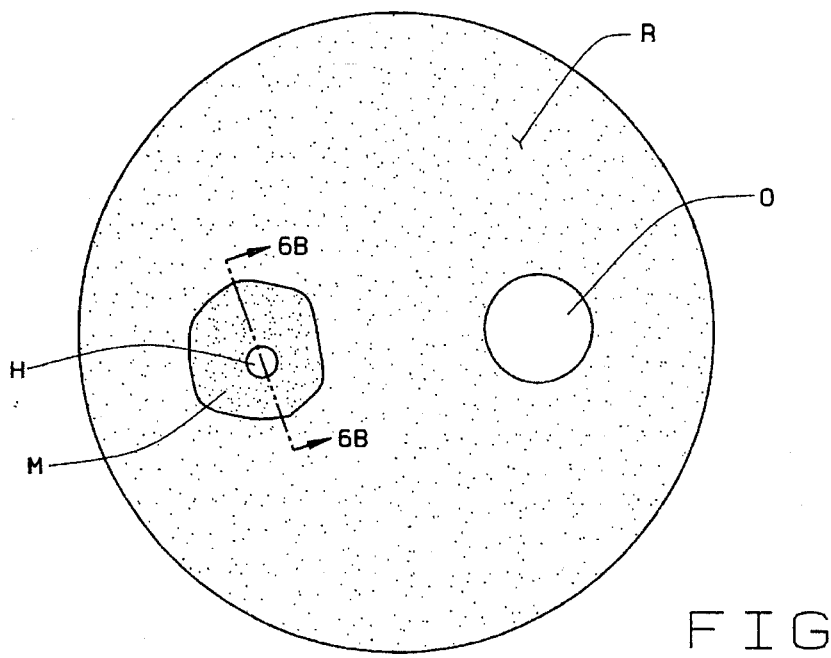
FIG. 6A
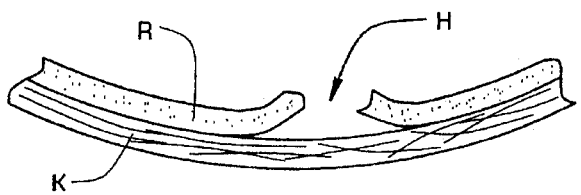
FIG. 6B

RETINAL PLUG

BACKGROUND OF THE INVENTION

This application is a continuation-in-part of application Ser. No. 08/284,906, filed Aug. 2, 1994.

This invention relates generally to ophthalmological surgery, and more specifically to a retinal plug used to repair retinal tissue and to a method of using the same.

Loss of retinal tissue occurs naturally as a result of the aging process or as a result of secondary changes within the vitreous cavity. For example, a loss of retinal tissue occurs as a result of the formation of traction bands that pull and tear the retina. Whatever the cause, retinal holes or retinal tears can lead to retinal detachment by the flow of vitreous fluid into the retinal space through the tear or hole. Furthermore, the loss of sensory retinal tissue exposes retinal pigment epithelial cells lying under the sensory retina to stimulating factors present in the vitreous fluids. Such exposure causes the cells to lose their underlying structures, migrate, and proliferate in the vitreous cavity and in the subretinal space. Proliferation of these pigmented epithelial cells will produce membrane on the surface of the retina or under the retina creating fix folds, which hold the retina in a detached position.

Detached retinas occur in a significant number of the population with the incidents varying between 0.01% to 2% or more, depending upon the underlying condition causing the retinal detachment. Retinal tears and holes are formed in older individuals as a result of the aging process. Generally, such tears and holes are located in the peripheral and posterior part of the retina, i.e. the macula. Moreover, a greater incidence of such tears and holes are formed in persons suffering from myopia, persons who have undergone cataract extraction, persons suffering from diabetic retinopathy, aids patients suffering from cytomegalic virus retinitis, and in persons suffering from trauma to the eye.

Until recently, there were two primary procedures for the treatment of retinal holes and tears. One treatment constitutes removal of the vitreous traction and tamponade the retina from inside the eye using gas, silicone, perfluorocarbon liquid or other appropriate procedures. A second treatment consists of bringing the wall of the eye closer to the retina from outside via the so called scleral buckling procedure. After the choroid or wall of the eye is drawn closer to the retina, cryo-coagulation or laser coagulation is applied adjacent the retina to create adhesion between the retina and the choroid. The process of cryo-coagulation or laser coagulation of the retina adjacent to the hole does not interfere with vision if the hole is located in the peripheral region of the eye. However, there can be a significant effect on the patient's vision if the tear is located in the posterior pole. Laser coagulation and cryo-coagulation damage the healthy retina located adjacent the retinal hole. There is a loss of visual acuity as a result of the destruction of the normal cells adjacent to the retinal hole. There is a significant loss of vision when the hole is near to the center of the macula, or in fact, when there is a hole in the macula.

It would be advantageous, therefore, to repair the retinal hole or tear to prevent ingress of fluid into the sub-retinal space. Such a procedure should protect the healthy retina located adjacent the retinal hole and preserve the patient's sight. Such a repair should employ a plug to cover the exposed retinal pigmented epithelial cells, and prevent the migration of such cells into the vitreous cavity. Such a plug can be a formed from a solid, semi-solid gel or liquid material.

SUMMARY OF THE INVENTION

It is, therefore, among the principal objects of the present invention to provide a retinal plug to repair a tear or hole in the retina;

It is another object of the invention to provide retinal patch that covers the entire area of a retinal defect;

Another object of the present invention to provide a retinal plug which can cover the exposed retinal pigmented epithelial cells to prevent the migration of such cells into the vitreous cavity;

Yet another object of the present invention is to provide a retinal plug made of a biodegradable material;

It is another object of the invention to provide a retinal plug which can be made out of a nonbiodegradable synthetic material;

Still another object of the invention is to provide a retinal plug which is made from an injectable liquid or gel material;

Another object of the present invention is to provide a method of filling a retinal defect with a retinal plug that will prevent the ingress of fluid into the subretinal space and prevent migration of retinal pigmented epithelial cells into the vitreous cavity.

In accordance with the invention, generally stated, a retinal plug is provided to repair a retinal defect. The retinal plug can be made from a solid or liquid biodegradable material, biodegradable synthetic material, a natural material, or a nonbiodegradable material. The biodegradable plug can be a disk made out of gelatin, fibrin, fibrin and collagen combination, elastin, chondroytin sulfate, hyaluronic acid, for example. A nonbiodegradable plug can be made out of cross-link collagen, chondroitin sulfate or a combination thereof, for example. The plug can be made of synthetic biodegradable materials such as polyglycolic acid, polylactic acid, polyanhydfide, and polycaprolactone, for example. A plug can be made out of a nonbiodegradable material such as silicone rubber, Dacron, or other material that does not incite tissue reaction when implanted into the eye. Preferably, the plug can be fiat, mushroom shaped, or configured like a button. Other configurations are compatible with the broader aspects of the invention. An injectable liquid plug can be made from a collagen solution.

A method of using the retinal plug includes performing a vitrectomy to remove the vitreous gel from the eye through a small incision made at the side of the pars plana; observing as the vitreous is removed and replacing the vitreous with a physiological solution; removing tractions and membranes from the surface of the retina or from under the retina; mattaching the retina by removing the fluid from the submtinal space and the vitreous cavity with the simultaneous injection of air into the vitreous cavity; and filling or covering the hole or tear in the retina with a retinal plug cut to fit the size of the hole in the retina. The plug is grasped by a small forceps and introduced through the previously made incision. The plug is positioned to fit the retinal defect. Prior to insertion, the plug can be trimmed and modified so that the plug fits the defect according to the size and shape of the defect. The retinal plug preferably has a thickness essentially equal to the thickness of the retina. In one illustrative embodiment of the invention the retinal plug has a mushroom shape wherein the stem portion fits inside the retinal defect and the head portion extends over the adjacent retinal structure. In another illustrative embodiment the plug can has a spool shape wherein one fiat surface rests on the outer surface of the retina and another fiat surface rests on the inner surface of the retina. In yet another illustrative embodiment, the plug is a very small amount of liquid gel collagen material injected over the retinal tear using a 200 microliter syringe with a small gauge needle. The liquid collagen gels at body temperature to form a plug. Furthermore, the plug can contain a cell stimulating substance such as platelet derived growth factor, epidermal growth factor, fibroblast growth factor, tissue growth factor beta, nerve growth factor, or other hormones such as somatostatin.

BRIEF DESCRIPTION OF THE DRAWINGS

FIG. 1 is an isometric view of illustrative embodiment of the retinal plug of the present invention;

FIG. 2 is a top plan of the retinal plug shown in FIG. 1;

FIG. 3 is a side elevational view of the retinal plug shown in FIG. 1;

FIG. 4 is a side elevational view of a second illustrative embodiment of the retinal plug of the present invention;

FIG. 5 is a third illustrative embodiment of the retinal plug of the present invention;

FIG. 6A is a front view of the posterior internal wall of the eyeball;

FIG. 6B is a section view along line 6B—6B of FIG. 6A;

DESCRIPTION OF THE PREFERRED EMBODIMENT

Figure 7:
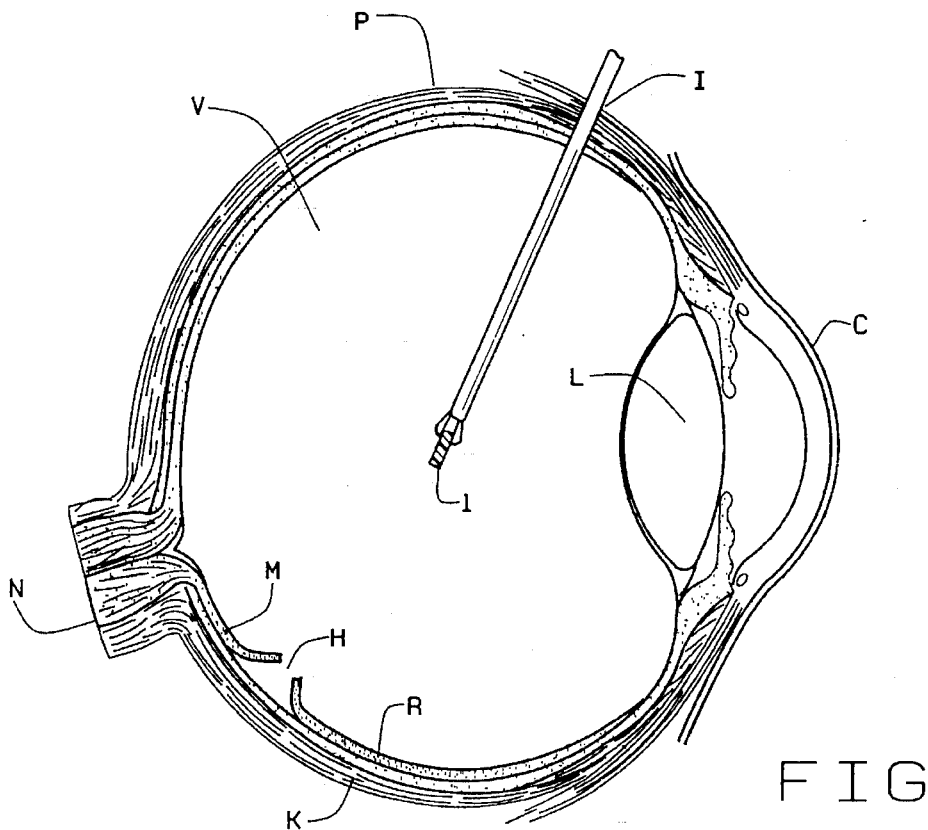
FIG. 7 is a cross-sectional view of an eyeball illustrating the method of using the retinal plug of the present invention.

One illustrative embodiment of retinal plug of the present invention is indicated generally by reference numeral 1 in FIGS. 1–3.

Plug 1, as illustrated, is a generally disk-like structure having opposed flat sides 3 and 5 with a material thickness T in between. Material thickness T is essentially equal to the thickness of the retina of the eye at the sight of the defect of the retina to be repaired.

Therefore, thickness T can vary from approximately 0.01 mm to 2.0 mm. The diameter D1 of plug 1 may vary, again depending upon the dimension of the defect to be repaired as will be explained below. Plug 1 can be extremely thin and dimensioned to cover a retinal defect rather than fit into the defects. In this configuration plug 1 would be positioned over the defect and function as a patch. However, it will be appreciated that plug 1 can be provided in any appropriate size and can be trimmed with a surgical scissors, for example, to fit the outline of the defect to be repaired. Plug 1 is illustrated in FIG. 1 and 2 as having fibers for clarity of illustration. Plug 1 can be constructed from a number of different materials depending upon the desired characteristics of the plug. For example, the plug can be constructed from a natural or synthetic material, a biodegradable or nonbiodegradable material, or a combination thereof. A biodegradable plug 1, which can be replaced by growing normal tissue to repair the defect in the retina, can be constructed from gelatin, fibrin, chondroitin sulfate or other acceptable biodegradable, physiologically compatible, material.

A nonbiodegradable or slowly biodegradable plug can be constructed from polymeric material of naturally occurring cross-linked fibrous material such as cross-linked collagen, fibrin, chondroitin sulfate, elastin, hyaluronic acid, glucosaminoglycan, or a mixture thereof.

Plug 1 also can be constructed from a synthetic biodegradable polymer material such as polyglycolic acid, polylactic acid, polyanhydride, polycaprolactone, or a mixture of these polymers.

Furthermore, Plug 1 can be constructed from a nonbiodegradable synthetic material such as silicone rubber, dacron, teflon, vinyl, or a mixture thereof. Other material compositions are compatible with the broader aspects of my invention.

FIG. 4 illustrates a second illustrative configuration of the plug of the present invention indicated generally by reference numeral 10. Plug 10 is generally mushroom shaped and has a stem 12 and cap 14. Stem 12 has a diameter D2 that preferably corresponds generally to the dimension of the defect or hole in the retina. Stem 12 is designed to fit into the hole. Cap 14 has a diameter D3 greater than the diameter D2 so that cap 14 extends beyond the defect and covers the surrounding retina as will be discussed below. Stem 12 has a material thickness between 0.01 mm and 2.0 mm, corresponding to the thickness of the surrounding retina.

FIG. 5 illustrates yet another illustrative embodiment of the retinal plug of the present invention indicated generally by reference numeral 20. Plug 20 has a spool configuration. Plug 20 has a first or upper annular flat section 22 and a second or lower annular flat section 24. The first and second flat sections are connected by a middle section 26. Middle section 26 has a material thickness T approximately that of the surrounding retina, i.e., 0.01 mm to 2.0 mm. The diameter D4 of middle section 26 is approximately the same as the hole in the retina to be repaired. Diameter D5 of the respective flat sections is greater than D4 so that the respective flat sections extend out and cover the periphery of the defect on both the outer and inner sides of the retina, as will be explained below.

It will be noted that the respective embodiments of the retinal plug are shown as having circular configurations for the sake of clarity of illustration. It will be appreciated, however, that any of the plugs can be provided in a variation of configurations and dimensions. For example, plug 1 can be provided as a rectangle rather than a disk and trimmed to correspond to an irregular outline of the retinal defect, either to fill the defect or cover the defect like a patch. Moreover, the dimensions of the retinal plug may vary depending upon the size of the defect to be repaired.

The retinal plug of the present invention can be impregnated with a cell stimulating substance to create adhesion of the surrounding tissue to the plug by stimulating cell migration into the plug material. Examples of such cell stimulating materials include hormones such as platelet derived growth factor, fibroblast growth factor, epidermal growth factor, tissue growth factor beta, nerve growth factor, somatostatin in, or any other appropriate cell stimulating substance.

Figure 8:
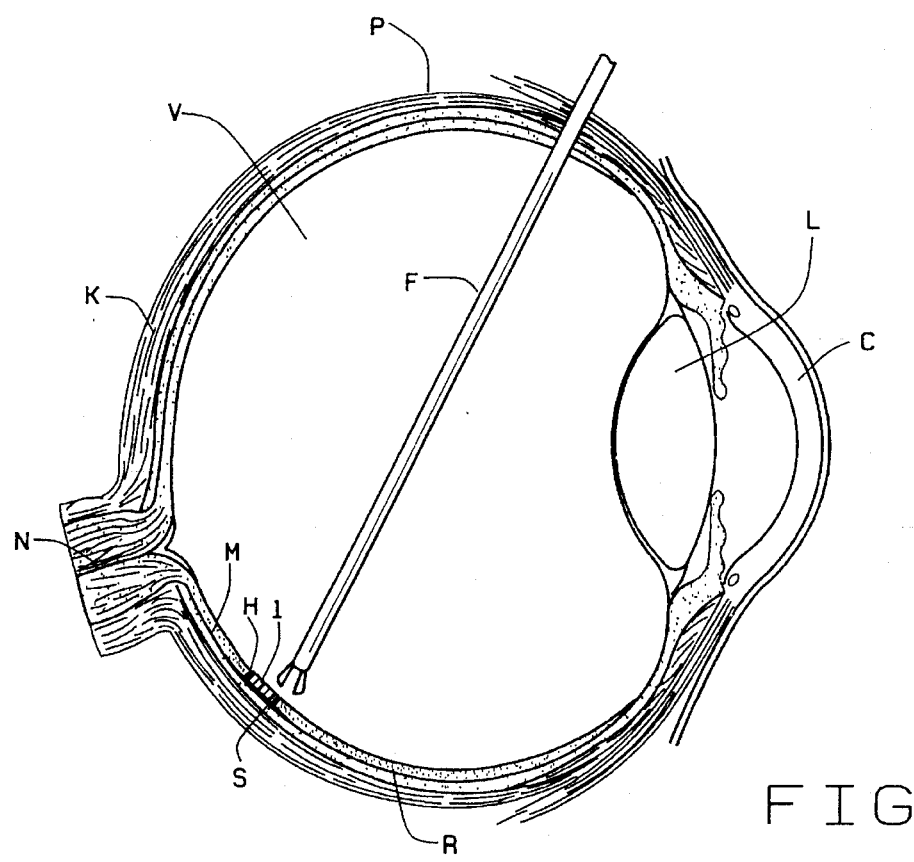
FIG. 8 is another cross-sectional view of an eyeball illustrating the method of using the retinal plug of the present invention.
Figure 9A:
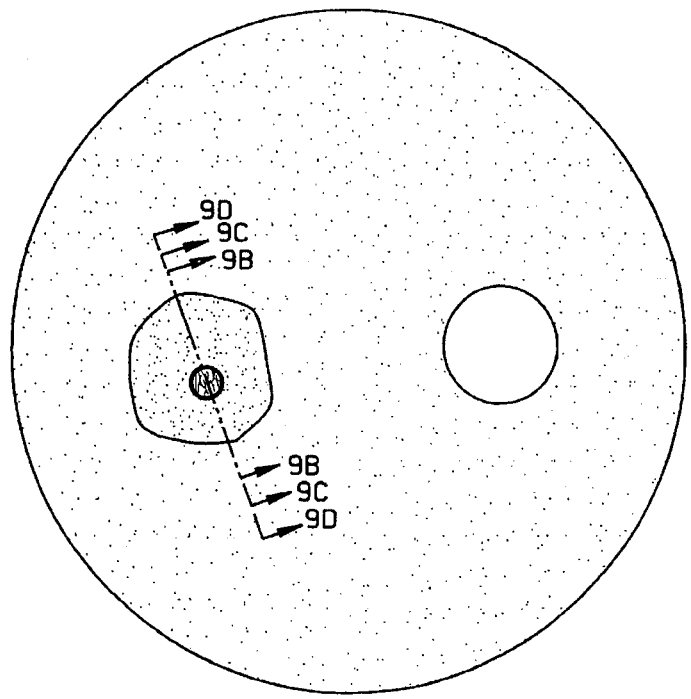
FIG. 9A is a front view of the posterior internal wall of the eyeball.
Figure 9B:
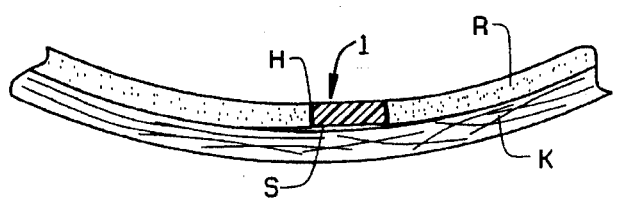
FIG. 9B is a sectional view taken along lines 9B—9B of FIG. 9A.

FIGS. 6A and 6B illustrate a reparable defect in the retina. FIGS. 7 and 8 illustrate the surgical application of retinal plug of the present invention. The anatomy of the eye is conventional and is not described in detail. The relevant anatomical landmarks in the eye include the vitrous cavity V, retina R, macula M, choroid K, cornea C, lens L, optic nerve N, and the optic disk D. The defect or hole in the macular area is shown generally as H. FIG. 7 illustrates a surgical technique of repairing a hole H with a plug 1. A vitrectomy is made through the pars plana P an incision I. Vitreous fluid, tractions and membranous material is removed. The removed vitreous material can be replaced with a physiological solution. Fluid is forced from the subretinal space and from the vitreous cavity V as routinely done in a number of known ways. Vitreous fluid simultaneously is replaced with air or gas to reattach the retina and to force any fluid or air bubbles out from behind retina R. The vitreous cavity V can be filled with gas, such as air, which is reabsorbed with time and replaced with the body fluid. Alternatively, the vitreous cavity V can be filled up with artificial material such as silicone, or perfluorocarbon to create a long-term tamponading effect. Regardless of the method of filling the vitreous cavity, plug 1, for example, is grasped by a forceps F and inserted through incision I. Plug 1 is placed in hole H with a tight fit as shown in FIG. 8. If plug 1 is configured to cover the defect like a patch, plug 1 is placed over the defect and surrounding tissue. FIGS. 9A through 9D illustrate the repaired hole H. FIG. 9B illustrates the hole H repaired with retinal plug 1. The plug 1 is contiguous with the surrounding retina R. Plug 1 fills the defect and prevents ingress of vitreous fluid into subretinal space S. This procedure protects the healthy retina R located adjacent to hole H and preserves the patient's sight. Moreover, the plug prevents exposed retinal pigmented cells from migrating into the vitreous cavity V and subsequent membrane formation.

Figure 9C:
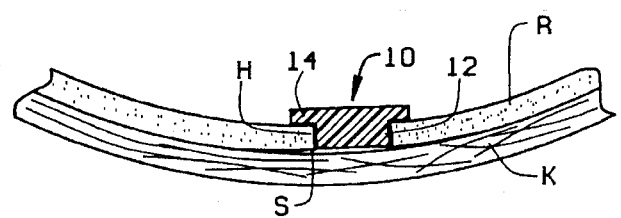
FIG. 9C is a sectional view taken along lines 9C—9C of FIG. 9A.

FIG. 9C illustrates insertion of retinal plug 10 into hole H. Stem 12 is inserted into the hole and cap 14 overlaps the retinal tissue like a patch. The embodiment, as illustrated by FIG. 9C, is particularly appropriate for plugging and patching a hole having uneven or jagged edges. Cap 14 overlays hole H and prevents the ingress of fluid and the egress of pigmented cells.

Figure 9D:
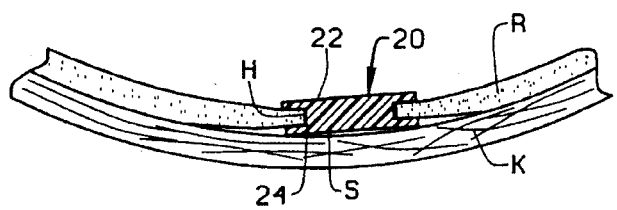
FIG. 9D is a sectional view taken along lines 9D—9D of FIG. 9A.

FIG. 9D illustrates the use of retinal plug 20 to plug hole H. As shown, flat section 24 as captured under the retina R and flat section 22 extends over the retina R. This embodiment is particularly effective for sealing hole H and preventing the ingress of vitreous fluid and the egress of pigmented cells. Plug 20 particularly is useful in treating defects in the retina where the retina is particularly thin and when it is difficult to get the plug to stay in the hole without this "buttoning" arrangement.

After insertion, plugs made from a biodegradable material will eventually dissolve and the surrounding retinal tissue can replace the dissolved plug.

Furthermore, if the plugs are impregnated with a cell stimulating agent as is described above, there will be enhanced proliferation of surrounding retinal tissue into the plug to facilitate biodegradation of the plug and adhesion of the retina to the underlying tissue.

Plugs constructed of a nonbiodegradable, such as teflon, will remain in the defect. However, the nonbiodegradable plug can be impregnated with cell stimulating agents to stimulate the proliferation of the surrounding tissue to overgrow the plug.

Figure 10:
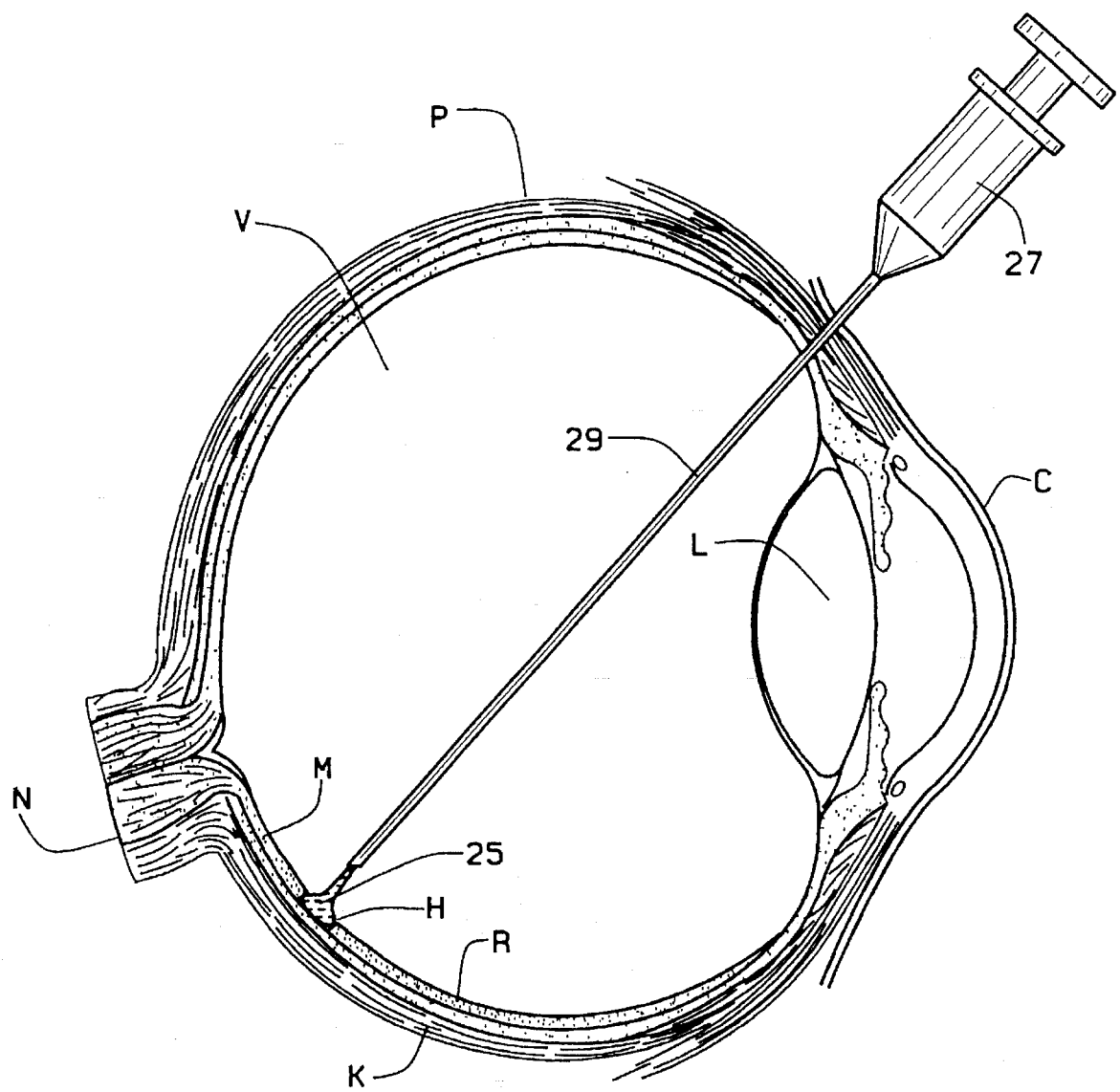
FIG. 10 is a cross-sectional view of an eyeball illustrating a method of injecting a liquid material to form a retinal plug of the present invention.

Another alternative embodiment of the present invention is illustrated in FIG. 10. In this embodiment, the plug is formed from a liquified material that is injected over the retinal tear or hole H and then forms a gel at body temperature.

One such material that gels at body temperature is a solubilized collagen solution. It will be appreciated that collagen is the principal structural protein in animals and is present in connective tissue. Twelve different types of collagen have been isolated, but the most important collagens are Types I, II and III. Collagen has a number of features that make it useful in this application. First, it has high tensile strength; second, biodegradation is controllable; third, it has hemostatic properties; fourth it has low antigenicity; and fifth, it rarely elicits inflammatory or cytotoxic reactions.

In one embodiment of FIG. 10, solubilized collagen is used and is based on telopeptide-poor xenogenie collagen in solution. This form of solubilized collagen remains in liquid form between 0° and 5° C. When heated to body temperature, i.e. 37° C., fibrils and cross-links form to convert the material to a semi-solid.

A liquid rat tail collagen is prepared by following the method described by Michaelopoulos and Pitore in "Primary Culture Of Parenchymal Liver Cells On Collagen Membranes", *Experimental Cell Research*, Vol. 78, 1975, pp. 70–78, which is hereby incorporated by reference. The acid-solubilized collagen was stored cold until use in a concentration of 0.3% to 0.9% w/v.

Gels were formed directly in a 1 ml plastic syringe by adding 1.5 ml of collagen to 0.35 ml of a 2:1 mixture of N-2-hydroxyethylpiperazine-N-2-ethanesulfonic acid (HEPES, UBS) buffer (50 mM HEPES, 0.75M NaCl, and 0.75M KCL) and 0.28M NaOH. Gelation was retarded by keeping the solution at <4°.

A solution 25, in the preferred embodiment, is a cold collagen solution 25 is drawn into a tuberculin or microliter syringe 27, having a 27 gauge needle 29. The needle 29 is inserted into the vitreous cavity V and brought close to the surface of the retina R over the hole H in the retina. The collagen solution 25 is injected onto the hole H. The eollagen solution 25 fills the hole. At body temperature, collagen solution 25 turns to a gel to form a plug in hole H.

In another embodiment of FIG. 10, the solution 25 is a low viscosity liquid ophthalmic latex that forms a gel in in-situ. Solution 25 is a pH-triggered ophthalmic latex which is a low-viscosity polymeric dispersion in water.

In yet another embodiment of FIG. 10, solution 25 is a polymer that changes from solution to gel at the temperature of the eye, i.e. 33° to 34° C. One such polymer is poloxamer F 127, which consists of ployoxyethylene and polyoxypropylene units. At room temperature the poloxamer remains a solution. At an elevated temperature, however, the solution becomes a gel.

In another embodiment of FIG. 10, the solution consists of a polysaccharide, low-acetyl gellan gum which forms a clear gel in the presence of mono or divalent cations. One such product is Gelrite®.

It will be appreciated that a vitrectomy and air-fluid exchange procedure can be performed prior to the injection of solution 25. In this procedure, the patient is appropriately positioned and the vitreous tissue is cut and suctioned using a vitrector. A non-expanding gas is injected and migrates to the tear. The injected gas urges the detached retinal tissue against the choroid C and forces fluid from behind the tear and the retinal tissue. The solution then is applied as described above.

It will be apparent to those skilled in the art that various modifications and changes can be made without the appending claims. Therefore, the foregoing description and drawings are intended to be illustrative only and should not be interpreted in a limiting sense.

What is claimed:

1. A method of plugging a hole in the retina of the eye comprising the steps of:

drawing a solution into a syringe, said syringe having a small bore needled thereon, the solution having a physical property so that it forms a gel at the temperature of the eye;

inserting said needle into the vitreous cavity of the eye;

positioning the tip of said needle over the hole in the retina;

injecting the solution on the hole in the retina; and allowing the solution to form a gel to plug the hole in the retina.

2. The method of claim 1 wherein the solution is a solubilized collagen.

3. The method of claim 1 wherein the solution is a low viscosity liquid ophthalmic latex.

4. The method of claim 1 wherein the solution is a polymer solution.

5. The method of claim 1 wherein the solution is a polysaccharide, low-acetyl gellan gum solution.

6. A method of repairing a defect in the retina comprising the steps of:

performing a vitrectomy;

reattaching the retina through the vitrectomy by removing fluid from the subretinal space and simultaneously injecting air into a vitreous cavity;

drawing a solution into a syringe, said syringe having a small bore needle thereon, said solution having a physical property whereby it gels at the temperature of the eye;

inserting the needle into the vitreal cavity of the eye;

positioning the tip of the needle over the retinal defect;

injecting the solution onto the retina defect; and allowing the solution to gel thereby forming a gel plug of the retinal defect.

* * * * *